United States Patent [19]
Saito et al.

[11] Patent Number: 6,107,506
[45] Date of Patent: Aug. 22, 2000

[54] PROCESS FOR PRODUCING 2-(2-HYDROXYPHENYL) PHENYLPHOSPHINIC ACID AND DERIVATIVES

[76] Inventors: Toranosuke Saito, c/o Sanko Kaihatsu Kagaku Kenkyusho Osaka Kenkyusho, 10-24, Itsukaichi 1-chome, Ibaraki-shi, Osaka, 567; Takumi Hirayama, c/o Sanko Kaihatsu Kagaku Kenyusho Shiga Kenkyusho, 657-1, Shimonogo-cho, Moriyama-shi, Shiga, 524; Yukinori Kohguchi, c/o Sanko Co., Ltd. Arao Factory, 1850, Masunaga, Arao-shi, Kumamoto, 864, all of Japan

[21] Appl. No.: 09/065,126

[22] Filed: Apr. 23, 1998

Related U.S. Application Data

[63] Continuation of application No. PCT/JP96/03114, Oct. 25, 1996.

[51] Int. Cl.$^7$ ............................. C07F 9/6574; C07F 9/30
[52] U.S. Cl. ................................. 558/82; 562/23
[58] Field of Search ................. 558/82; 562/23

[56] References Cited

U.S. PATENT DOCUMENTS

| | | | |
|---|---|---|---|
| 3,702,878 | 11/1972 | Saito | 558/82 |
| 5,481,017 | 1/1996 | Kleiner | 558/82 |
| 5,650,530 | 7/1997 | Buysch et al. | 558/82 |

FOREIGN PATENT DOCUMENTS

| | | |
|---|---|---|
| 2 034 887 | 1/1972 | Germany . |
| 47-16436 | 9/1972 | Japan . |
| 49-45397 | 12/1974 | Japan . |
| 1 547 105 | 6/1979 | United Kingdom . |

*Primary Examiner*—Michael G. Ambrose

[57] ABSTRACT

In the coexistence of an a 5~20 molar excess of water based upon 2-phenylphenol compound which is reacted with phosphorus trihalide to form a 6-halo-(6H)-dibenzo[c.e][1,2]-oxaphosphorin compound and an organic solvent which is unsoluble in water and is inert in the reaction system, an organic phosphorus compound expressed by the structural formula (1) is hydrolyzed under heating to obtain a biphenyl phosphorus compound expressed by the general formula (2) and then, a cyclising dehydration reaction under heating of the resulting compound is carried out to obtain an organic phosphorus compound expressed by the structural formula (3). This constitution can produce a product of high purity and high quality without using specific chemicals or an equipment made of specific materials.

8 Claims, No Drawings

PROCESS FOR PRODUCING 2-(2-HYDROXYPHENYL) PHENYLPHOSPHINIC ACID AND DERIVATIVES

This application is a continuation of PCT International Application No. PCT/JP96/03114, filed Oct. 25, 1996.

FIELD OF THE INVENTION

This invention relates to a process for producing a biphenyl phosphorus compound expressed by the general formula (2)

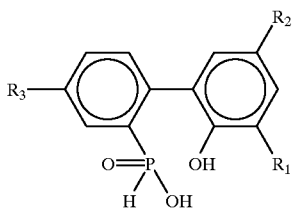

(2)

wherein $R_1$, $R_2$ and $R_3$ which may be the same or different are hydrogen, a halogen atom, an alkyl group, a cycloalkyl group, an aryl group or an aralkyl group
and a cyclic organic phosphorus compound expressed by the general formula (3)

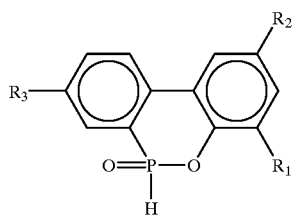

(3)

wherein $R_1$, $R_2$ and $R_3$ are the same as defined in the general formula (2) and more particularly, relates to a process for producing the end products of high purity and high quality.

BACKGROUND OF THE INVENTION

The compound expressed by the general formula (3) is used as a stabilizer and a fire retardant for organic low molecular weight and high molecular weight compounds, and also, is used as a quality-improving material and a yield-improving material in production of these compounds. This compound is an important material that is used as a raw material in production of many stabilizers, fire retardants and retardative organic high molecular weight compounds.

The compound expressed by the general formula (2) is important as a raw material for production of the compound expressed by the general formula (3), and also, is important as a raw material in production of stabilizers and fire retardants for organic low molecular weight and high molecular weight compounds. Both the compounds are expected furthermore to extend their use in the future.

For producing the compounds expressed by the general formula (2) and general formula (3), there is known a conventional process which comprises heat-condensing a o-phenyl phenol compound expressed by the general formula (4)

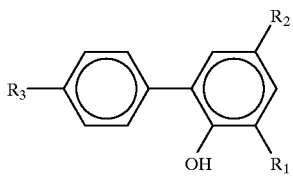

(4)

wherein $R_1$, $R_2$ and $R_3$ are the same as defined in the general formula (3) and a phosphorus trihalide expressed by the general formula (5)

$$PX_3 \quad (5)$$

wherein X is chlorine or bromine in the presence of Friedel Crafts catalyst to produce a compound expressed by the general formula (1)

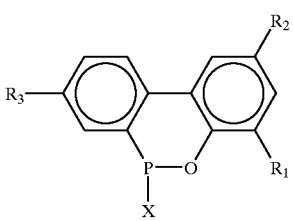

(1)

wherein $R_1$, $R_2$, $R_3$ and X are the same as defined in the general formula (4) and (5), pouring the resulting compound into the excess amount of water, followed by and hydrolysing under heating and precipitating under cooling, or pouring the resulting compound into an aqueous solution of an alkali metal hydroxide, hydrolysing under heating, acid-precipitating after cooling to produce a compound expressed by the general formula (2), followed by cyclising-dehydrating under heating to produce a compound expressed by the general formula (3) (see, for example, Japanese patent publications Nos. Sho 45397/1974 and Sho 17979/1975).

Also, there is proposed a process of producing a compound expressed by the general formula (3) by hydrolysing a compound expressed by the general formula (1) with equivalent mol of water in the presence of organic solvent (see Japanese Patent Laid Open No. Hei 145185/1995).

However, in case that the compounds expressed by the general formula (2) and the general formula (3) obtained by such processes are used as the stabilizers and fire retardants for organic low molecular weight and high molecular weight compounds, particularly in case of using as electronic materials and synthetic fibers, further in case of using as a semiconducter-sealing and a raw material of high molecular weight compounds for producing synthetic fibers, the compounds of high purity and high quality are required, so that the products obtained by the conventional processes are difficult to satisfy these requirements.

Therefore, there were attempted purification methods such as vacuum-distillation purification before hydrolysis or recrystalization purification by an inert organic solvent in case of a compound expressed by the general formula (1), or acid-precipitation purification after active carbon treatment of aqueous solution of an alkali metal hydroxide, or recrystalization by the mixed solution of alcohol and water in case of a compound expressed by the general formula (3). However, since either purification has a problem in the yield and/or is insufficient in removal of inorganic and/or organic impurities, the aim has not been attained so far.

An object of the present invention is to provide a product of high purity and high quality without using an alkali or a particular chemical, a complicated operation such as vacuum distillation or an equipment made of specific materials.

DISCLOSURE OF THE INVENTION

According to the present invention, there is provided a process for producing a biphenyl phosphorus compound expressed by the general formula (2)

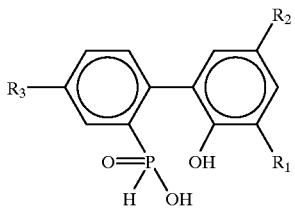

(2)

wherein $R_1$, $R_2$ and $R_3$ which may be the same or different are hydrogen, a halogen atom, an alkyl group, a cycloalkyl group, an aryl group or an aralkyl group, which comprises hydrolysing a compound expressed by the general formula (1)

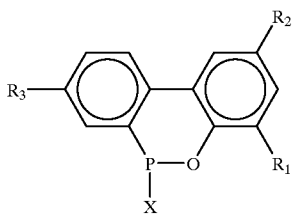

(1)

wherein X is chlorine or bromine; $R_1$, $R_2$ and $R_3$ are the same as defined in the general formula (2) in the presence of an organic solvent which is insoluble in water and is inert in the reaction system and a 5~20 molar excess of water based upon 2-phenylphenol compound which is reacted with phosphorus trihalide to form a 6-halo-(6H)-dibenzo[c.e][1,2]-oxaphosphorin compound under normal pressure or elevated pressure, followed by washing the organic solvent layer with water.

Further, according to the present invention, there is provided a process for producing a cyclic organic phosphorus compound expressed by the general formula (3), which comprises cyclic-dehydrating of a compound expressed by the general formula (2). Thus, the cyclic organic phosphorus compound of high purity and high quality can be produced by this process.

BEST MODE OF EMBODIMENTS OF THE INVENTION

The present invention will be further described by way of preferred embodiments.

A cyclic organic phosphorus compound expressed by the structural formula (1A) (hereinafter referred to as CC)

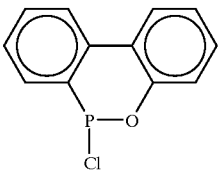

(1A)

is prepared by heat-condensation reaction of o-phenyl phenol expressed by the structural formula (4A) (hereinafter referred to as OPP)

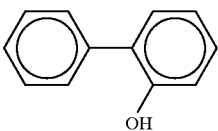

(4A)

in the coexistance of a phosphorus trichloride expressed by the structural formula (5A)

$PCl_3$ (5A)

and a zinc chloride catalyst.

Mol ratio of OPP and the phosphorus trichloride is about 1:1~2, preferably about 1:1.1~1.5.

The amount of the catalyst used is about 0.05~3 parts by weight (hereinafter referred to "part"), preferably about 0.1~1 parts to 100 parts of OPP.

Reaction temperature is about 30~250° C., preferably about 50~230° C., and a hydrogen chloride gas is generated with proceeding of reaction, and the temperature is raised to nearly 210° C. at last. The termination of hydrogen generation may be regarded as the end of reaction.

Reaction time is 3~35 hours, preferably 5~15 hours, depending on other reaction condition such as the reaction temperature and the amount of catalyst used. However, if the reaction is prosecuted suddenly, the hydrogen chloride gas is generated in large quantities and the accompanying loss of phosphorus trichloride may be caused and it is undesirable in view of safety in operation.

After completion of condensation reaction, the reaction mixture is cooled to 80~90° C., and added with an organic solvent which is insoluble in water and is inert in the reaction system (hereinafter referred to as a solvent), preferably under stirring to dissolve the reaction mixture. The amount of the solvent is about 30~100 parts, preferably about 40~70 parts to 100 parts of OPP.

This mixed solution is cooled to about 35° C. or less and then gradually poured into the liquid mixture of water and solvent with stirring. At this time the temperature is elevated 15~30° C. At this time the amount of water is a 5–20 molar excess of water based upon OPP, the amount of solvent is about 50~1000 parts, preferably about 100~500 parts to 100 parts of OPP. After pouring, the temperature of the contents is raised under stirring to carry out the hydrolysation at the reflux temperature. The time of hydrolysis reaction is about 1~10 hours, preferably about 2~5 hours if necessary, according to a type of the solvent and/or its amount, the hydrolysis reaction temperature is elevated to quicken the hydrolysis reaction velocity or/and to prevent the precipitation of hydrolysis product.

After the completion of the hydrolysis reaction, the reaction liquid mixture is cooled to 60~90° C. and allowed to stand, followed by separation of a water layer and then, water of 60~80° C. is added to an oil layer and stirred and allowed to stand, followed by separation of liquid. This washing operation is repeated preferably 3 times. The amount of warm water is 0.2~1 times the reaction liquid mixture, preferably about 0.3~0.6 times. According to a type of the solvent and/or its amount, the hydrolysed product may be precipitated, in this case, the hydrolysation operation being carried out preferably, under elevated pressure. According to a type of the solvent and/or its amount, the degree of elevating the pressure is preferably about 1~10 m aqueous pillar.

After water-washing, a residual moisture of the oil layer is removed by azeotropic distillation, and the decoloration treatment is conducted at 70~80° C. (about 1% of activated carbon and/or activated clay to OPP), and after filtration 30~100 parts, preferably 40~70 parts of water is added to cool about 25° C. or less, followed by filtration and washing of the precipitates to obtain white crystalline, wet filtration mass. According to the measurement by infrared absorption spectrum analysis and the elemental analysis, this material is identified to be a OPP compound expressed by the structural formula (2A)

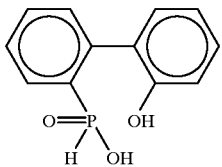

(2A)

(hereinafter referred to as HBP).

Then, for this wet filtration mass, a cyclic dehydration reaction is carried out under reduced pressure at 110~180° C., and water adhered was removed between room temperature and about 80° C., and the temperature was gradually raised, and the cyclising dehydration reaction is carried out at 110~160° C. The cyclising dehydration reaction is carried out at 120~160° C./100 mmHg for about 1~10 hours, preferably for about 1~3 hours.

After the cyclising dehydration reaction, the contents are poured out to a enameled bat at nealy 120° C., cooled and roughly pulverized to obtain a white crystalline, rough granular substance. By the elemetal analysis and the infrared absorption spectrum analysis, this material is identified to be a cyclic organic phosphorus compound expressed by the structural formula (3A) (hereinafter referred to as HCA).

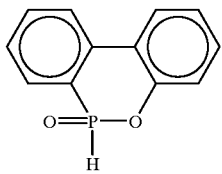

(3A)

As another dehydration method, an inert organic solvent which is azeotropic with usual water, particularly the organic solvent aftermentioned and a biphenyl phosphorus compound expressed by the general formula (2) are heated and subjected to heat to azeotropic dehydration. Thus, the cyclising dehydration reaction of a biphenyl phosphorus compound expressed by the general formula (2) is proceeded effectively as well as residual water in the reaction mixture solution and it is confirmed that a cyclic organic phosphorus compound expressed by the structural formula (3) is produced. In this case, the azeotropic dehydration temperature is preferably about 100~130° C., and if necessary, according to a type of solvent, the azeotropic point is regulated by increasing or reducing the pressure.

By the measurement of melting point, melting color, liquid chromatography analysis and microanalysis of the chlorine and zinc contents, HBP and HCA obtained in such a manner are confirmed to be extremely high purity and high quality.

OPP compounds expressed by the general formula (4) are exemplified wherein $R_1$, $R_2$ and $R_3$ are given by ($R_1=R_2=R_3=H$), ($R_1=Cl,R_2=R_3=H$), ($R_1=Br,R_2=R_3=H$), ($R_1=R_2=Cl, R_3=H$), ($R_1=R_2=Br,R_3=H$), ($R_1=R_2=R_3=Cl$), ($R_1=R_2=R_3=Br$), ($R_1=CH_3,R_2=R_3=H$), ($R_1=R_2=CH_3,R_3=H$), ($R_1=R_2=R_3=CH_3$), ($R_1=octyl,R_2=R_3=H$), ($R_1=cyclohexyl,R_2=R_3=H$), ($R_1=R_3=H,R_2=phenyl$), ($R_1=benzyl,R_2=R_3=H$) and ($R_1=R_3=H, R_2=\alpha,\alpha$-dimethylbenzyl etc.

Instances of the phosphorus trichloride expressed by the general formula (5A) are exemplified by phosphorus trichloride and phosphorus tribromide.

Instances of the organic solvent which is insoluble in water and is inert in the reaction system include toluene, o-, m-, p-xylene, chlorobenzene, o-dichlorobenzene and dichloroethane etc.

The present invention is illustrated by the following examples.

EXAMPLE 1

Into a 500-ml reactor equipped with an agitator, a thermometer and a reflux condenser which is connected to a gas outlet treatment equipment are introduced 204 gr (1.2 mols) of o-phenylphenol, 140 gr of phosphorus trichloride and 1.2 gr of zinc chloride and are gradually heated. When the temperature of the contents has been raised to about 30° C., the contents is fused. At this point the agitator is actuated. Further the contents is gradually heated to 180~200° C., 66 gr (total 206 gr, 1.5 mols) of phosphorus trichloride is gradually added, and in about 8 hours the thermometer reached 210° C. Generation of hydrogen chloride gas terminates, followed by cooling the condensation reaction product to 100° C., adding 120 gr of chlorobenzene, and further cooling the product to about 30° C. Into a reactor equipped with a reflux condenser and containing 240 gr of water and 600 gr of chlorobenzene, the above reaction liquid mixture is gradually added with stirring. The temperature of the contents has been raised from about 20° C. to about 65° C. The contents is further heated and hydrolysed at condensation temperature for 3 hours.

Thereafter, the reaction liquid mixture is allowed to stand while holding at 70~80° C. and separated a water layer (the reaction water layer separated) and 120 gr of warm water of 50~60° C. are added to an oil layer and stirred for about 1 hour and are allowed to stand at the same temperature and separated a water layer (the washed water layer separated). This operation is repeated at 3 times. Thereafter, the water isolated from the oil layer is azeotropic dehydrated, and 2.6 gr of activated clay is added at 70~80° C. to conduct the decoloring filtration, and 60 gr of water is added to cool to 25° C. or less and precipitates is filtered out and washed with cold water to obtain a white crystalline, wet filtration mass. This material is a compound of $R_1=R_2=R_3=H$ (hereinafter referred to as HBP) of the compounds expressed by the general formula (2), and it has a purity 99.9% or higher by liquid chromatography analysis.

This wet filtration mass is heated to 105~110° C. and fused and the pressure is gradually reduced and finally, the cyclising dehydration reaction is carried out at 80~100 mmHg and 120~130° C. for 2 hours. After completion of the generation of water, the contents is poured into a enameled bat, cooled and roughly pulverized to obtain a white crystalline, rough granular substance. By the measurement of elemental analysis and infrared absorption spectrum analysis, this material is identified to be a compound of $R_1=R_2=R_3=H$ of the compounds expressed by the general formula (3) (hereinafter referred to as HCA). Yield: 249 gr. Yield (calculated value based on OPP): 94%. M.P. 118° C. Purity by liquid chromatography analysis: 99.9% or higher. OPP content: trace. Zn content: 1 ppm or less. Cl content: 1 ppm. Na content: 1 ppm or less.

The reaction water layer separated and the washing water layer separated are cooled to 20° C. or less and precipitates are filtrated to obtain 8.4 gr of HBP (conversion to HCA: 7.8 gr, yield based on OPP: 3%). HCA total yield: 97%.

EXAMPLE 2

Using 301 gr of 2-cyclohexyl-6-phenylphenol in place of 204 gr of OPP in Example 1, the operation is carried out in the same manner described in Example 1 to obtain 331 gr of white crystalline, rough granular substance of the compound of $R_1$=cyclohexyl, $R_2$=$R_3$=H of the compounds expressed by the general formula (3). Yield: 93%. Purity: 99.9%. M.P. 163° C. 2-cyclohexyl-6-phenylphenol content: trace. Cl content: 1 ppm. Zn content: 1 ppm or less. Na content: 1 ppm or less.

EXAMPLE 3

The condensation reaction product mixture which is obtained by the operation in the same manner described in Example 1 is cooled to about 100° C., followed by adding 120 gr of toluene, and cooling further to about 30° C. Into a reactor equipped with a reflux condenser containing 240 gr of water and 600 gr of chlorobenzene, the above reaction liquid mixture is gradually added with stirring, and the contents is heated to be hydrolysed at condensation temperature for about 3 hours. Thereafter, the reaction liquid mixture is washed 3 times with 150 ml/time of acid aqueous solution of a hydrochloric acid and 2 times with 150 ml/time of water at 80~90° C. under elevated pressure (4 m aqueous pillar), followed by changing a reflux condenser for a streaming condenser, carrying out the ring-closing reaction by azeotropic-dehydration under heating and normal pressure to change HBP for HCA, and when the temperature of content mixture reached about 115° C., azeotropic streaming has already terminated. The decoloring filtration of the contents mixture is carried out with 2.6 gr of activated clay, followed by cooling to about 5° C. to filter out precipitates, washing with toluene and drying to obtain 251.1 gr of white powder. M.P. 118° C. By the measurement of elemental analysis and infrared absorption spectrum analysis, this material is identified to be HCA. Purity: 99.9%. OPP, Zn, Cl and Na content is each 1 ppm or less. Yield (calculated value based on OPP): 88%. 28.5 g of HCA is contained in the incorporated liquid of filtrate (filtering out precipitates) and washing liquid of toluene, and 279.6 gr of the total amount which contains the beforementioned isolation HCA is correspond to 98% of yield (calculated value based on OPP).

Comparable Example 1

The condensation reaction product mixture which is obtained by the operation in the same manner described in Example 1 is cooled to about 100° C., and poured into 1700 gr of 8.5%-sodium hydroxide solution with stirring. And the temperature of the liquid mixture poured has been raised from 25° C. to 70° C. for pouring. After about 1 hour of stirring, the resulting compound is regulated to pH 4.5 by diluted sulfuric acid, and 15 gr of activated carbon is added and stirred at 50~60° C. for 0.5 hour and the filtration is carried out. The filtrate is acidified to pH 1.5 by diluted sulfuric acid at 25° C. or less and filter out precipitates and washed to obtain HCA of a white crystalline, rough granular. Yield: 233 gr, Yield: 90%. M.P. 117~118° C. Purity: 99.3%. OPP content: 4000 ppm. Cl content: 100 ppm. Zn content: 7 ppm. Na content: 200 ppm.

Comparable Example 2

The condensation reaction product mixture which is obtained by operating in the same manner described in Example 1 is held at nearly 210° C. and under reduced pressure of 1 mmHg with stirring, followed by removing a hydrogen chloride gas and a phosphorus trichloride. The resulting compound is cooled to about 100° C., and 220 gr of chlorobenzene is added and the temperature is held at about 70° C. 216 gr (1.2 mols) of water is added to the above compound for 6 hours and gradually heated to react at condensation temperature for 9~10 hours. After generation of hydrogen chloride gas has terminated and the reaction finished, followed by cooling the reaction mixture to about 100° C., adding 350 gr of chlorobenzene as an addition, adding 1.5 gr of activated clay for decoloring treatment and filtration at 70~80° C., filtering precipitates and washed with chlorobenzene, and drying under reduced pressure at 25° C. or less to obtain HCA of white crystalline powder. Yield: 246 gr. Yield: 95%. Purity: 98.5%. M.P. 115~117° C. OPP content: 20 ppm. Cl content: 40 ppm. Zn content: 30 ppm.

APPLICABILITY FOR INDUSTRIAL USE

The compound expressed by the general formula (3) is used as a stabilizer and a fire retardant for organic low molecular weight and high molecular weight compounds, and also, is used as a quality-improving material and a yield-improving material in production of these compounds. This compound is an important material that is used as a raw material for production of many stabilizers, fire retardants and retardative organic high molecular weight compounds.

The compound expressed by the general formula (2) is important as a raw material for production of the compound expressed by the general formula (3), and also, is important as a raw material for production of stabilizers and fire retardants for organic low molecular weight and high molecular weight compounds. Both the compounds are expected furthermore to extend their use in the future.

The present invention can produce an end phosphorus compound with high yield, high purity and high quality and in particular, the content of byproducts of an inorganic and organic compound is extremely low and also, there is no need to use specific chemicals or equipments made of specific materials for production and the operation is also easy.

What we claim is:

1. A process for producing a biphenyl phosphorus compound expressed by the general formula (2)

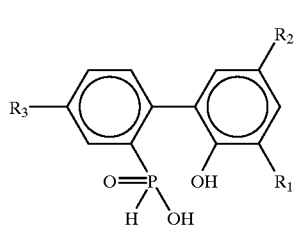

(2)

wherein $R_1$, $R_2$ and $R_3$ which may be the same or different are hydrogen, a halogen atom, an alkyl group, a cycloalkyl group, an aryl group or an aralkyl group, which comprises hydrolysing a cyclic organic phosphorus compound expressed by the general formula (1)

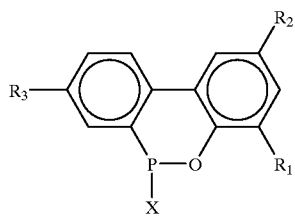

(1)

wherein X is chlorine or bromine, and $R_1$, $R_2$ and $R_3$ are the same as defined in the general formula (2), in the presence of an organic solvent which is insoluble in water and is inert in the reaction system and 5~20 molar equivalents of water (based upon a 2-phenylphenol compound which is reacted with phosphorus trihalide to form the 6-halo-(6H)-dibenzo [c.e][1,2]-oxaphosphorin compound of formula (1)) under normal pressure or elevated pressure, followed by washing the resulting organic solvent layer with water to obtain the compound expressed by the general formula (2).

2. A process for producing a cyclic organic phosphorus compound expressed by the general formula (3)

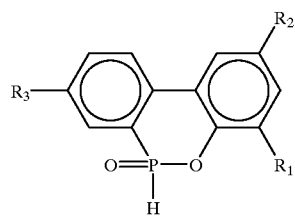

(3)

wherein $R_1$, $R_2$ and $R_3$, which may be the same or different, are hydrogen, a halogen atom, an alkyl group, a cycloalkyl group, an aryl group or an aralkyl group, which comprises hydrolyzing a cyclic organic phosphorus compound expressed by the general formula (1)

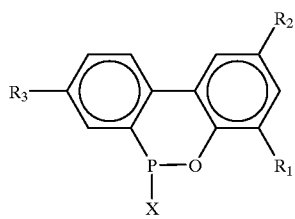

(1)

wherein X is chlorine or bromine, and $R_1$, $R_2$ and $R_3$ are the same as defined in the general formula (3), in the presence of an organic solvent which is insoluble in water and is inert in the reaction system and 5~20 molar equivalents of water (based upon a 2-phenylphenol compound which is reacted with phosphorus trihalide to form the 6-halo-(6H)-dibenzo [c.e][1,2]-oxaphosphorin compound of formula (1)) under normal pressure or elevated pressure to obtain the biphenyl phosphorus compound expressed by the general formula (2)

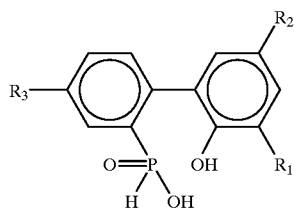

(2)

wherein $R_1$, $R_2$ and $R_3$ are the same as defined in the general formula (3), then washing the organic solvent layer containing said biphenyl phosphorus compound with water, and carrying out a cyclising dehydration reaction of said biphenyl phosphorus compound to obtain the compound expressed by the general formula (3).

3. The process for producing a cyclic organic phosphorus compound expressed by the general formula (3) according to claim 2, wherein said biphenyl phosphorus compound expressed by the general formula (2) is isolated from an organic solvent layer washed with water after the hydrolysis reaction in claim 2 and then, a cyclising dehydration under heating is carried out.

4. The process for producing a cyclic organic phosphorus compound expressed by the formula (3) according to claim 2, wherein the cyclising dehydration under heating of said biphenyl phosphorus compound expressed by the general formula (2) is carried out by azeotropic dehydration.

5. A process for producing a biphenyl phosphorus compound expressed by the general formula (2)

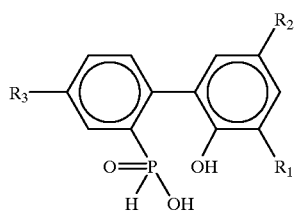

(2)

wherein $R_1$, $R_2$ and $R_3$, which may be the same or different, are hydrogen, a halogen atom, an alkyl group, a cycloalkyl group, an aryl group or an aralkyl group, which comprises carrying out a condensation reaction between a o-phenyl phenol compound expressed by the general formula (4)

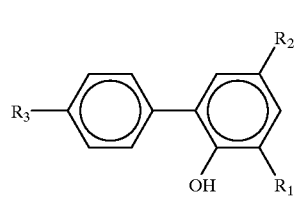

(4)

wherein $R_1$, $R_2$ and $R_3$ are the same as defined in the general formula (2), and a phosphorus trihalide expressed by the general formula (5)

$PX_3$ (5)

wherein X is chlorine or bromine, in the presence of Friedel Crafts catalyst to obtain a 6-halo-(6H)-dibenzo[c.e][1,2]-oxaphosphorin compound expressed by the general formula (1)

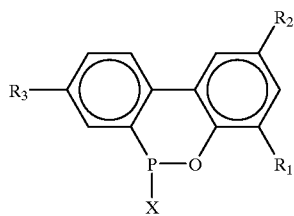
(1)

wherein X is chlorine or bromine, $R_1$, $R_2$ and $R_3$ are the same as defined in the general formula (2) and then, hydrolyzing said cyclic organic phosphorus compound in the presence of an organic solvent which is insoluble in water and is inert in the reaction system and 5~20 molar equivalents of water based upon the 2-phenylphenol compound of formula (4) under normal pressure or elevated pressure, followed by washing the resulting organic solvent layer with water to obtain the compound expressed by the general formula (2).

6. A process for producing a cyclic organic phosphorus compound expressed by the general formula (3)

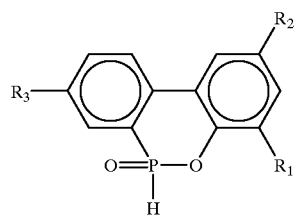
(3)

wherein $R_1$, $R_2$ and $R_3$, which may be the same or different, are hydrogen, a halogen atom, an alkyl group, a cycloalkyl group, an aryl group or an aralkyl group, which comprises carrying out a condensation reaction between a o-phenyl phenol compound expressed by the general formula (4)

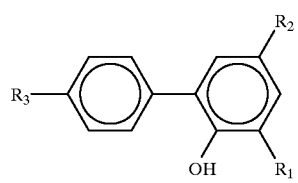
(4)

wherein $R_1$, $R_2$ and $R_3$ are the same as defined in the general formula (3), and a phosphorus trihalide expressed by the general formula (5)

PX$_3$ (5)

wherein X is chlorine or bromine, in the presence of Friedel Crafts catalyst to obtain a 6-halo-(6H)-dibenzo[c.e][1,2]-oxaphosphorin compound expressed by the general formula (1)

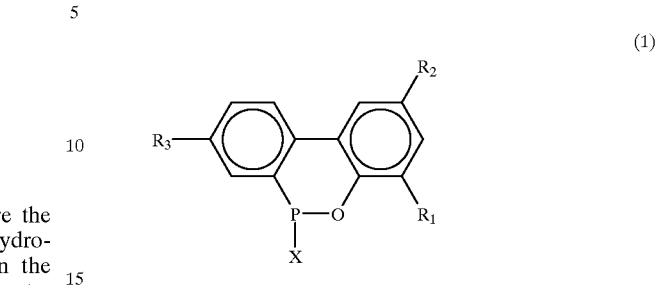
(1)

wherein X is chlorine or bromine, and $R_1$, $R_2$ and $R_3$ are the same as defined in the general formula (3), hydrolyzing said cyclic organic phosphorus compound in the presence of an organic solvent which is insoluble in water and is inert in the reaction system and 5~20 molar equivalents of water based upon the 2-phenylphenol compound of formula (4) under normal pressure or elevated pressure to obtain the biphenyl phosphorus compound expressed by the general formula (2)

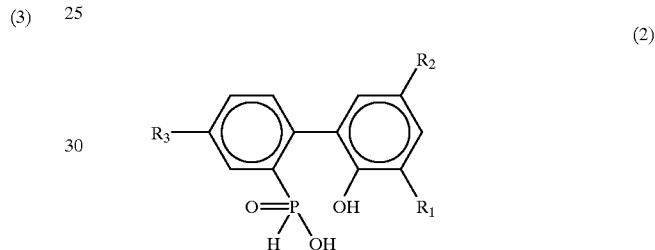
(2)

wherein $R_1$, $R_2$ and $R_3$ are the same as defined in the general formula (3) and then, washing the organic solvent layer containing said biphenyl phosphorous compound with water, followed by carrying out a cyclising dehydration reaction of said biphenyl phosphorus compound to obtain the compound expressed by the general formula (3).

7. The process for producing a cyclic organic phosphorus compound expressed by the general formula (3) according to claim 6, wherein said biphenyl phosphorus compound expressed by the general formula (2) is isolated from an organic solvent layer washed with water after the hydrolysis reaction in claim 6 and then, a cyclising dehydration under heating is carried out.

8. The process for producing a cyclic organic phosphorus compound expressed by the formula (3) according to claim 6, wherein the cyclising dehydration under heating of said biphenyl phosphorus compound expressed by the general formula (2) is carried out by azeotropic dehydration.

* * * * *

UNITED STATES PATENT AND TRADEMARK OFFICE
CERTIFICATE OF CORRECTION

PATENT NO. : 6,107,506
DATED : August 22, 2000
INVENTOR(S) : Toranosuke Saito, Takumi Hirayama and Yukinori Kohguchi It is certified that error appears in the above-identified patent and that said Letters Patent is hereby corrected as shown below:

Title page,
The following should be added:
-- [73] Assignee: Sanko Kaihatsu Kagaku Kenkyusho, Osaka Japan --
The following should be added:
-- [30] Foreign Application Priority Data
    Oct. 27, 1995 [JP] Japan .................... 280249/1995
    Apr. 17, 1996 [JP] Japan .................... 095089/1996 --

Signed and Sealed this

Fourteenth Day of August, 2001

*Attest:*

*Attesting Officer*

NICHOLAS P. GODICI
*Acting Director of the United States Patent and Trademark Office*